United States Patent [19]
Barley, Jr.

[11] Patent Number: 5,306,490
[45] Date of Patent: Apr. 26, 1994

[54] METHODS FOR RETARDING BLISTER FORMATION BY USE OF CYANOACRYLATE ADHESIVES

[75] Inventor: Leonard V. Barley, Jr., Colorado Springs, Colo.

[73] Assignee: Medlogic, Inc., Colorado Springs, Colo.

[21] Appl. No.: 871,558

[22] Filed: Apr. 20, 1992

[51] Int. Cl.$^5$ .................. A61L 25/00; A61L 15/24; A61K 31/78

[52] U.S. Cl. .................. 424/78.35; 424/78.02; 424/78.08; 128/889; 128/893; 523/111; 602/52; 602/54; 602/904; 526/936

[58] Field of Search ............ 424/78.27, 78.35, 78.02, 424/78.05, 78.08, 443, 445; 602/42, 52, 54, 904; 604/304; 523/111; 526/298, 936; 428/522, 908.8; 156/330.9; 128/889–893

[56] References Cited

U.S. PATENT DOCUMENTS

| | | | |
|---|---|---|---|
| 2,804,073 | 8/1957 | Galliene et al. | 128/156 |
| 3,527,224 | 9/1970 | Rabinowitz | 526/297 |
| 3,591,676 | 7/1971 | Hawkins et al. | 424/78.06 |
| 3,667,472 | 6/1972 | Halpern | 128/334 R |
| 3,995,641 | 12/1976 | Kronenthal et al. | 558/400 |
| 4,035,334 | 7/1977 | Davydov et al. | 424/78.06 |
| 4,444,933 | 8/1984 | Columbus et al. | 524/292 |
| 4,650,826 | 3/1987 | Waniczek et al. | 524/730 |
| 4,958,748 | 9/1990 | Otake | 222/108 |

OTHER PUBLICATIONS

Chem Abstr CA 479-027521(05) Akers et al.
Akers, Arch. Dermatol., vol. 107, pp. 544–547, (Apr. 1973).
Bhaskar, Surindar N. et al., "Healing of Skin Wounds with Butyl Cyanoacrylate", pp. 294–297, 1969, Journal of Dental Research, vol. 48, No. 2.
Dalvi, A. et al., "Non-suture Closure of Wound Using Cyanoacrylate", pp. 97–100, 1986, Journal of Postgraduate Medicine, vol. 32, No. 2.
Eiferman, Richard A. et al., "Antibacterial Effects of Cyanoacrylate Glue", pp. 958–960, Jun. 1983, Archives of Ophthalmology, vol. 101.
Ellis, David A. f. et al., "The Ideal Tissue Adhesive in Facial Plastic and Reconstructive Surgery", pp. 68–72, 1990, The Journal of Otolaryngology, vol. 19, No. 1.
Fung, Ramona Q. et al., "Use of Butyl-2-Cyanoacrylate in Rabbit Auricular Cartilage", pp. 459–464, Jul. 1985, Archives of Otolaryngology, vol. 111.
Galil, K. A. et al., "The Healing of Hamster Skin Ulcers Treated with N-butyl-2-cyanoacrylate (Histoacryl blue)", pp. 601–607, 1984, Journal of Biomedical Materials Research, vol. 18.
Harper, Marion C., "Stabilization of Osteochondral Fragments Using Limited Placement of Cyanoacrylate in Rabbits", pp. 272–276, Jun. 1988, Clinical Orthopaedics and Related Research 231.
Kamer, Frank M. et al., "Histoacryl: Its Use in Aesthetic Facial Plastic Surgery", pp. 193–197, Feb. 1989, Archives of Otolaryngology Head and Neck Surgery, vol. 115.
Kosko, Paul I., "Upper Lid Blepharoplasty: Skin Closure Achieved with Butyl-2-Cyanoacrylate", pp. 424–425, Jun. 1981, Ophthalmic Surgery, vol. 12.
Lehman, Ralph A. W. et al., "Toxicity of Alkyl 2-Cyanoacrylate: Bacterial Growth", pp. 447–450, Sep. 1966, Archives of Surgery, vol. 93.
Leonard, Fred et al., "Synthesis and Degradation of Poly(alkyl-1-Cyanoacrylate)", pp. 259–272, 1966, Journal of Applied Polymer Science, vol. 10.
Makady, F. M. et al., "Effect of tissue adhesives and suture patterns on experimentally induced teat lacerations in lactating dairy cattle", pp. 1932–1934, Jun. 1991, JAVMA, Reports of Original Studies, vol. 198, No. 11.
Matsumoto, Teruo, "Bacteriology and Wound Healing", pp. 106–113, 1972, Chapter 3 in Tissue Adhesives in Surgery.

(List continued on next page.)

Primary Examiner—Edward Webman
Attorney, Agent, or Firm—Burns, Doane, Swecker & Mathis

[57] ABSTRACT

A cyanoacrylate adhesive is applied to the skin areas prone to blistering prior to blister formation.

13 Claims, No Drawings

OTHER PUBLICATIONS

Matsumoto, Teruo, "Clinical Considerations and Applications of Bucrylate Tissue Adhesive", pp. 226-237, 1972, Tissue Adhesives in Surgery, Chap. 1, Sec. III.

Matsumoto, Teruo, "Reactions of the Organism to Acrylate-Adhesives", pp. 436-444, 1972, Tissue Adhesives in Surgery.

Matsumoto, Teruo et al., "Tissue Adhesive and Wound Healing", pp. 266-271, Mar. 1969, Archives of Surgery, vol. 98.

Mizrahi, S. et al., "Use of Tissue Adhesives in the Repair of Lacerations in Children", pp. 312-313, Apr. 1988, Journal of Pediatric Surgery, vol. 23, No. 4.

Morton, R. J. et al., "The Use of Histoacryl Tissue Adhesive for the Primary Closure of Scalp Wounds", pp. 110-112, 1988, Archives of Emergency Medicine, vol. 5.

Ousterhout, D. K. et al., "Cutaneous Absorption of n-Alkyl-1-Cyanoacrylate", pp. 157-163, 1968, Journal of Biomedical Materials Research, vol. 2.

Pepper, D. C., "Kinetics and Mechanism of Zwitterionic Polymerization of Alkyl Cyanoacrylate", pp. 629-637, 1980, Polymer Journal, vol. 12, No. 9.

Pepper, David Charles et al., "Kinetics of Polymerization of Alkyl Cyanoacrylate by Tertiary Amines and Phosphines", pp. 395-410, 1983, Makromol. Chem., vol. 184.

Ronis, Max L. et al., "Review of Cyanoacrylate Tissue Glues with Emphasis of Their Otorhinolaryngological Applications", pp. 210-213, Feb. 1984, Larngoscope., vol. 94.

Saches, Michael Evan., "Enbucrylate as Carilage Adhesive in Augmentation Rhinoplasty", pp. 389-393, Jun. 1985, Archives of Otolaryngology, vol. 111.

Toriumi, Dean M. et al., "Histotoxicity of Cyanoacrylate Tissue Adhesives: A Comparative Study", pp. 546-550, Jun. 1990, Archives of Otolaryngology Head and Neck Surgery, vol. 116.

Tseng, Yin-Chao et al., "Modification of Synthesis and Investigation of Properties for 2-cyanoacrylate", pp. 73-79, Jan. 1990, Biomaterials, vol. 11.

Vinters, H. V. et al., "The Histotoxicity of Cyanoacrylate: A Selective Review", pp. 279-291, 1985, Neuroradiology, vol. 27.

Watson, David P., "Use of Cyanoacrylate Tissue Adhesive for Closing Facial Lacerations in Children", p. 1014, Oct. 1989, British Medical Journal, vol. 299.

METHODS FOR RETARDING BLISTER FORMATION BY USE OF CYANOACRYLATE ADHESIVES

BACKGROUND OF THE INVENTION

1. Field of the Invention

The present invention is directed to methods for retarding blister formation by use of cyanoacrylate adhesives that can be applied to skin areas prone to blistering prior to blister formation.

2. State of the Art

Cyanoacrylate adhesives have been suggested for a variety of adhesive purposes including glues and surgical adhesives. In particular, cyanoacrylate adhesives of formula I:

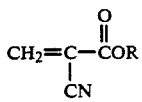

wherein R is an alkyl or other suitable substituents are disclosed in U.S. Pat. Nos. 3,527,224; 3,591,676; 3,667,472; 3,995,641; 4,035,334; and 4,650,826. Typically, when used as adhesives for living tissues, the R substituent is alkyl of from 2 to 6 carbon atoms and most often is butyl.

The suggested medical uses for cyanoacrylate adhesives have been limited to surgical environments wherein the cyanoacrylate adhesive are utilized as an alternative to sutures and are employed in a sterile environment. Specifically, in surgical environments, the cyanoacrylate adhesive is applied to separate sections of soft tissue. The cyanoacrylate adhesive, in the presence of water found in soft tissue, bonds to the skin as well as polymerizes so as to join separate sections of soft tissue together.

SUMMARY OF THE INVENTION

The present invention, generally speaking, is a result of the discovery that application of cyanoacrylate adhesives to blister prone areas and subsequent polymerization results in the formation of an artificial callus over the blister prone area thereby retarding the formation of blisters in these areas. More particularly, the application of cyanoacrylate adhesives is only to the surface of the skin and not to cut area of skin.

Thus, it can be understood that the present invention is directed to methods for inhibiting blister formation by application of a cyanoacrylate adhesive to the skin area prone to blistering prior to blister formation. Accordingly, in one of its method aspects, the present invention is directed to a method for inhibiting blister formation which comprises:

applying, prior to blister formation, a quantity of a cyanoacrylate adhesive to an area of skin which is prone to blister formation, which quantity of cyanoacrylate adhesive is sufficient to permit formation of an artificial callus; and maintaining the cyanoacrylate adhesive under conditions that permit the adhesive to polymerize so as to form an artificial callus which adheres to the area where the adhesive was applied, wherein the cyanoacrylate, in monomeric form, is represented by formula I:

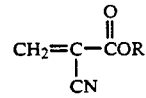

where R is selected from the group consisting of alkyl of 1 to 10 carbon atoms, alkenyl of 2 to 10 carbon atoms, cycloalkyl groups of from 5 to 8 carbon atoms, phenyl, 2-ethoxyethyl, 3-methoxybutyl, and a substituent of the formula:

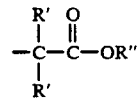

where each R' is independently selected from the group consisting of hydrogen and methyl and R" is selected from the group consisting of alkyl of from 1 to 6 carbon atoms; alkenyl of from 2 to 6 carbon atoms; alkynyl of from 2 to 6 carbon atoms; cycloalkyl of from 3 to 8 carbon atoms; aralkyl selected from the group consisting of benzyl, methylbenzyl and phenylethyl; phenyl; and phenyl substituted with 1 to 3 substituents selected from the group consisting of hydroxy, chloro, bromo, nitro, alkyl of 1 to 4 carbon atoms, and alkoxy of from 1 to 4 carbon atoms.

Preferably R is alkyl of from 1 to 10 carbon atoms and more preferably alkyl of from 2 to 6 carbon atoms. Most preferably, R is n-butyl.

In another of its method aspects, the present invention is directed to a method for inhibiting blister formation which comprises:

applying prior to blister formation at least 0.02 milliliter (ml) of cyanoacrylate adhesive per square centimeter of skin which is prone to blister formation; and maintaining the cyanoacrylate adhesive under conditions which permit the adhesive to polymerize so as to form an artificial callus which adheres to the are where the adhesive was applied wherein the cyanoacrylate, in monomeric form, is represented by formula II:

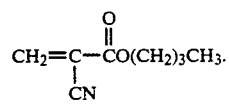

In a preferred embodiment, the cyanoacrylate adhesive to be applied to the skin has a viscosity of from about 2 to about 1000 centipoise at 20° C. More preferably, the cyanoacrylate adhesive is in monomeric form and has a viscosity of from about 2 to about 20 centipoise at 20° C.

As used herein, the following terms have the following meanings:

The term "cyanoacrylate adhesive" refers to adhesives based on cyanoacrylate monomers of formula I:

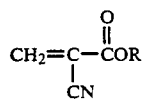

where R is selected from the group consisting of alkyl of 1 to 10 carbon atoms, alkenyl of 2 to 10 carbon atoms, cycloalkyl groups of from 5 to 8 carbon atoms, phenyl, 2-ethoxyethyl, 3-methoxybutyl, and a substituent of the formula:

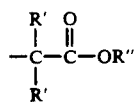

where each R' is independently selected from the group consisting of hydrogen and methyl and R'' is selected from the group consisting of alkyl of from 1 to 6 carbon atoms; alkenyl of from 2 to 6 carbon atoms; alkynyl of from 2 to 6 carbon atoms; cycloalkyl of from 3 to 8 carbon atoms; aralkyl selected from the group consisting of benzyl, methylbenzyl and phenylethyl; phenyl; and phenyl substituted with 1 to 3 substituents selected from the group consisting of hydroxy, chloro, bromo, nitro, alkyl of 1 to 4 carbon atoms, and alkoxy of from 1 to 4 carbon atoms.

Preferably, R is an alkyl group of from 1 to 10 carbon atoms including methyl, ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl and most preferably, R is n-butyl.

These cyanoacrylate adhesives are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

The term "artificial callus" refers to a layer of polymerized cyanoacrylate adhesive formed over and strongly adhering to a defined surface area of skin.

The term "blister" refers to an elevation of the epidermis containing a watery liquid which arises from friction during physical exertion as opposed to some type of disease condition (e.g., chicken pox). Contrarily, the term "blister" does not refer to irritated skin are as which have not yet blistered (i.e., formed a watery liquid under the epidermis). In this invention, the cyanoacrylate adhesive can be applied to irritated skin areas prior to blister formation as a means for preventing further irritation and, thereby, for retarding blister formation.

DETAILED DESCRIPTION OF THE REFERRED EMBODIMENT

The cyanoacrylate adhesive to be applied onto the skin can be monomeric or partially polymeric. In general, partially polymerized cyanoacrylate adhesives are liquid polymers having a higher viscosity than that of the corresponding monomer and, therefore, are better suited for those applications which are intended to be specific for a particular skin area. In other words, less viscous materials are more likely to "run" (i.e., flow) into areas where application was not intended.

The cyanoacrylate adhesives used herein preferably have a viscosity of from about 2 to about 1000 centipoise and more preferably from about 2 to about 20 centipoise at 20° C. The specific viscosity of the formulation depends on the amount and degree of partially polymerized cyanoacrylate adhesive employed. Such factors are readily ascertainable by the skilled artisan. For example, methods for preparing partially polymerized cyanoacrylate adhesives are disclosed, for example, by Rabinowitz, U.S. Pat. No. 3,527,224 which is incorporated herein by reference in its entirety.

Monomeric forms of cyanoacrylate adhesives are often preferred where application is to be made to a large surface. This preference results from the fact that those forms are less viscous and, accordingly, will permit more facile large surface area application. Mixtures of monomeric forms of cyanoacrylate adhesive and partially polymerized forms of cyanoacrylate adhesive can also be used to prepare a formulation having intermediate viscosities.

Upon contact with skin moisture, the cyanoacrylate adhesives will polymerize or, in the case of partially polymerized cyanoacrylate adhesives, will further polymerize, at ambient conditions (skin temperature) over 10 seconds to 60 seconds to provide for a solid layer which forms over and strongly adheres to the surface of the skin. This polymer layer serves as an artificial callus and protects the underlying skin against blistering in much the same way as does a natural callus.

The artificial callus, because of its strong binding affinity to skin and because of the durability of the polymerized cyanoacrylate adhesive serves as a substitute for human calluses.

In general, sufficient cyanoacrylate adhesive is applied onto the surface of the skin to provide for an artificial callus having sufficient thickness to inhibit blister formation. In a preferred embodiment, the artificial callus has a thickness of at least about 0.1 millimeter (mm) and more preferably at least about 0.3 mm. In another preferred embodiment, the artificial callus has a thickness ranging from about 0.1 mm to about 0.5 mm and even more preferably from about 0.1 to 0.3 mm. Normally, thicknesses greater than about 0.5 mm are not preferred because shearing forces may disrupt the adhesive formed.

In another preferred embodiment, the artificial callus is preferably formed by application of at least 0.02 ml of cyanoacrylate adhesive per square centimeter of skin.

Various parts of the human body are prone to blister formation, including the grip portions of hands and the base of feet. During physical exertion these parts of the body can be subject to friction by such activities as walking/jogging (feet), shoveling (hands). The all too familiar result of such activities, particularly in people not accustomed to such activities, is the formation of blisters in those areas prone to blister formation.

Formulations

The cyanoacrylate adhesive formulations employed herein generally comprise monomeric and/or partially polymerized compounds of formula I described above. These compositions are liquid in nature and, upon contact with skin moisture will polymerize to provide a solid film or layer over the skin surface.

The formulations may additionally contain one or more optional additives such as colorants, perfumes, and stabilizers. In practice, each of these optional additives should be both miscible and compatible with the cyanoacrylate adhesive. Compatible additives are those that do not prevent the use of the cyanoacrylate adhesives for their intended use.

In general, colorants are added so that the polymerized film will contain a discrete and discernable color. Perfumes are added to provide a pleasant smell to the formulation. Stabilizers are added to minimize in situ polymerization in containers during storage. Each of these additives are conventional. For example, suitable stabilizers are disclosed in U.S. Pat. No. 4,650,826 the disclosure of which is incorporated herein by reference in its entirety.

The formulation is generally stored in an applicator for use in a single dose application or for use in repeated applications. Single dose applicators include those having breakable or removable seals that prevent moisture, including atmospheric moisture, from contacting the formulation and causing in situ polymerization.

For repeated and intermittent usage, minimal exposure to atmospheric moisture is required. This can be achieved by devices having very narrow outlets and low initial deadspace. One applicator for such repeated intermittent use is described in U.S. Pat. No. 4,958,748 which is incorporated herein by reference.

In applicators suitable for repeated intermittent uses, the cyanoacrylate adhesive is stored at ambient conditions and is selected to be bacteriostatic. See, for example, Rabinowitz et al., U.S. Pat. No. 3,527,224. When the selected adhesive is bacteriostatic, prolonged storage at ambient conditions is without regard to the sterility of the formulation because there is no adverse buildup of bacteria during storage.

Methodology

The above-described formulations are applied onto the skin surface area under conditions suitable for polymerizing the adhesive so as to form an artificial callus. In general, sufficient amounts of cyanoacrylate adhesive are employed to permit formation of an artificial callus having a sufficient thickness to inhibit blister formation. In a preferred embodiment, the artificial callus has a thickness of at least about 0.1 mm and more preferably at least about 0.3 mm. Such artificial calluses are formed by applying at least about 0.02 ml of cyanoacrylate adhesive per square centimeter of skin surface area.

In another preferred embodiment, the amount of cyanoacrylate adhesive employed does not exceed about 0.05 ml per square centimeter. At concentrations in excess of that maximum preferred concentration, it can, in some cases, take too long for the artificial callus to form and the resulting callus is subject to shear forces. Additionally, higher concentrations of adhesive create polymers having less than desirable skin adherence and durability characteristics.

The amount of cyanoacrylate adhesive applied onto the skin surface area can be controlled by the amount of adhesive packaged in a single dose product or by use of a multiple use dispenser which governs the amount of material applied onto the skin. In this regard, the dispenser described by Otake, U.S. Pat. No. 4,958,748, which is incorporated by reference in its entirety, is particularly advantageous because it dispenses the adhesive in a controlled dropwise manner.

For inhibiting the formation of blisters, the cyanoacrylate adhesive is applied prior to blister formation. That is, the cyanoacrylate adhesive is applied onto the blister prone areas of the skin prior to initiation of physical activity which would be expected to result in the formation of blisters. Additionally, the cyanoacrylate adhesive can be applied onto blister prone areas at some point during physical activity when blister prone areas begin exhibiting some of the classic signs of blister formation (i.e., irritation, perceived heat and so forth).

Upon application of the cyanoacrylate adhesive, the surface skin moisture and temperature are sufficient to initiate polymerization of the adhesive upon application. Thereafter, the skin surface is maintained under suitable conditions to allow polymerization to proceed to formation of an artificial callus.

In general, the particular length of time required for polymerization will vary depending on factors such as the amount of adhesive applied, the temperature of the skin, the moisture content of the skin and the like. However, in a preferred embodiment, polymerization is generally complete in about 10 seconds and in about 60 seconds while the skin is maintained at ambient conditions. During this period, the person to whom application of the cyanoacrylate adhesive has been made merely allows the adhesive to form a callus while minimizing any action to prevent the adhesive from being dislodged from that portion of the skin where it was applied (e.g., washing his hands, placing socks on his feet) or to adhere to unintended objects (e.g., gripping an object immediately after application of the adhesive). After the artificial callus has formed, the callus strongly adheres to the skin, is flexible and waterproof thereby permitting the person to conduct the intended to activity.

In general, the artificial callus will adhere to the skin for a period of about 2-3 days after which time it sloughs off. However, if it is desirable to remove the artificial callus prior to it sloughing off, the artificial callus can be removed with acetone (nail polish remover).

It can now be understood that the methods of this invention are useful in retarding the formation of blisters. In particular, the methods of this invention result in the formation of artificial calluses which inhibit blister formation. As such, the methods of this invention are particularly suited for retarding blister formation in people who are prone to blister formation.

The following example illustrates certain embodiments of the invention but is not meant to limit the scope of the claims in any way.

EXAMPLE 1

A cyanoacrylate adhesive formulation was prepared in monomeric form using n-butyl α-cyanoacrylate of formula II above. The formulation was placed into the dispensing device described by Otake, U.S. Pat. No. 4,958,748. Three drops of the formulation were placed dropwise onto the palm of the hand in an area prone to blister formation of about 2 square centimeters in area so as to provide about 0.02 ml of adhesive per square centimeter. The hand was held palm up for about 1 minute. At this time an artificial callus had formed over this surface.

From the foregoing description, various modifications and changes in the composition and method will occur to those skilled in the art. All such modifications coming within the scope of the appended claims are intended to be included therein.

What is claimed is:

1. A method for inhibiting blister formation arising from friction during physical activities which method comprises:

applying, either prior to or during physical activities but prior to blister formation, a quantity of cyanoacrylate adhesive to a surface area of unbroken skin which is prone to blister formation, which quantity of cyanoacrylate adhesive is sufficient to form an artificial callus of from about 0.1 to about 0.5 millimeters in thickness; and polymerizing the cyanoacrylate adhesive so as to form an artificial callus which callus adheres to the surface area of unbroken skin where the adhesive was applied;

wherein the cyanoacrylate, in monomeric form, is represented by formula I:

$$CH_2=C(CN)-COR \quad \text{I}$$

where R is selected from the group consisting of alkyl of 1 to 10 carbon atoms, alkenyl of 2 to 10 carbon atoms, cycloalkyl groups of from 5 to 8 carbon atoms, phenyl, 2-ethoxyethyl, 3-methoxybutyl, and a substituent of the formula:

$$-C(R')(R')-C(=O)-OR''$$

where each R' is independently selected from the group consisting of hydrogen and methyl and R" is selected from the group consisting of alkyl of from 1 to 6 carbon atoms; alkenyl of from 2 to 6 carbon atoms; alkynyl of from 2 to 6 carbon atoms; cycloalkyl of from 3 to 8 carbon atoms; aralkyl selected from the group consisting of benzyl, methylbenzyl and phenylethyl; phenyl; and phenyl substituted with 1 to 3 substituents selected from the group consisting of hydroxy, chloro, bromo, nitro, alkyl of 1 to 4 carbon atoms, and alkoxy of from 1 to 4 carbon atoms.

2. A method according to claim 1 wherein R is alkyl of from 2 to 6 carbon atoms.

3. A method according to claim 2 wherein R is butyl.

4. A method according to claim 3 wherein R is n-butyl.

5. The method according to claim 1 wherein the cyanoacrylate adhesive has a viscosity of from about 2 to about 1000 centipoise at 20° C.

6. The method according to claim 5 wherein the cyanoacrylate adhesive has a viscosity of from about 2 to about 20 centipoise at 20° C.

7. The method of claim 1 wherein the cyanoacrylate adhesive is applied at a concentration of from about 0.02 ml to about 0.05 ml per square centimeter of surface area of uncut skin.

8. The method of claim 1 wherein the cyanoacrylate adhesive is polymerized by maintaining the cyanoacrylate adhesive on the uncut skin surface for a period of from about 10 to 60 seconds and at ambient skin temperature.

9. A method for inhibiting blister formation arising from friction during physical activities which method comprises:

applying, either prior to or during physical activities but prior to blister formation, from about 0.02 ml to about 0.05 ml of cyanoacrylate adhesive per square centimeter of surface area of unbroken skin which is prone to blister formation; and polymerizing the cyanoacrylate adhesive so as to form an artificial callus of from about 0.1 to about 0.5 millimeters in thickness which callus adheres to the surface area of unbroken skin where the adhesive was applied wherein the cyanoacrylate, in monomeric form, is represented by formula II:

$$CH_2=C(CN)-CO(CH_2)_3CH_3.$$

10. The method according to claim 9 wherein the cyanoacrylate adhesive has a viscosity of from about 2 to about 1000 centipoise at 20° C.

11. The method according to claim 10 wherein the cyanoacrylate adhesive has a viscosity of from about 2 to about 20 centipoise at 20° C.

12. The method of claim 9 wherein the cyanoacrylate adhesive is polymerized by maintaining the cyanoacrylate adhesive on the uncut skin surface for a period of from about 10 to 60 seconds and at ambient skin temperature.

13. A method for inhibiting blister formation arising from friction during physical activities which method comprises:

applying, either prior to or during physical activities but prior to blister formation, from about 0.02 to about 0.05 ml of cyanoacrylate adhesive per square centimeter of surface area of unbroken skin which is prone to blister formation, which quantity of cyanoacrylate adhesive is sufficient to form an artificial callus of from about 0.1 to about 0.5 millimeters in thickness; and polymerizing the cyanoacrylate adhesive by maintaining the cyanoacrylate adhesive on the unbroken skin surface for a period of from about 10 to 60 seconds and at ambient skin temperature so as to form an artificial callus which callus adheres to the surface area of unbroken skin where the adhesive was applied;

wherein the cyanoacrylate, in monomeric form, is represented by formula I:

$$CH_2=C(CN)-COR \quad \text{I}$$

where R is selected from the group consisting of alkyl of 1 to 10 carbon atoms, alkenyl of 2 to 10 carbon atoms, cycloalkyl groups of from 5 to 8 carbon atoms, phenyl, 2-ethoxyethyl, 3-methoxybutyl, and a substituent of the formula:

$$-C(R')(R')-C(=O)-OR''$$

where each R' is independently selected from the group consisting of hydrogen and methyl and R" is selected from the group consisting of alkyl of from 1 to 6 carbon atoms; alkenyl of from 2 to 6 carbon atoms; alkynyl of from 2 to 6 carbon atoms; cycloalkyl of from 3 to 8 carbon atoms; aralkyl selected from the group consisting of benzyl, methylbenzyl and phenylethyl; phenyl; and phenyl substituted with 1 to 3 substituents selected from the group consisting of hydroxy, chloro, bromo, nitro, alkyl of 1 to 4 carbon atoms, and alkoxy of from 1 to 4 carbon atoms.

* * * * *